(12) United States Patent
Nygaard et al.

(10) Patent No.: US 10,209,200 B2
(45) Date of Patent: Feb. 19, 2019

(54) HIGH-SPEED, 3-D METHOD AND SYSTEM FOR OPTICALLY INSPECTING PARTS

(75) Inventors: Michael G. Nygaard, Fenton, MI (US); Gregory M. Nygaard, Clarkston, MI (US)

(73) Assignee: Gil Acquisition, LLC, Davisburg, MI (US)

( * ) Notice: Subject to any disclaimer, the term of this patent is extended or adjusted under 35 U.S.C. 154(b) by 873 days.

(21) Appl. No.: 13/414,081

(22) Filed: Mar. 7, 2012

(65) Prior Publication Data

US 2013/0235371 A1 Sep. 12, 2013

(51) Int. Cl.
*G01N 21/00* (2006.01)
*G01N 21/88* (2006.01)
*G01N 21/952* (2006.01)
*G01N 21/95* (2006.01)

(52) U.S. Cl.
CPC ....... *G01N 21/8851* (2013.01); *G01N 21/952* (2013.01); *G01N 21/9515* (2013.01); *G01N 2201/0415* (2013.01); *G01N 2201/102* (2013.01)

(58) Field of Classification Search
CPC .............. G01N 21/00; G01N 21/8851; G01N 21/9515; G01N 21/952; G01N 2201/0415; G01N 2201/102; G06K 9/00; G02B 27/10
USPC ................ 356/237.2, 237.1; 382/152; 427/8; 359/627; 73/865.8
See application file for complete search history.

(56) References Cited

U.S. PATENT DOCUMENTS

| | | |
|---|---|---|
| 4,831,251 A | 5/1989 | Hanna |
| 5,383,021 A | 1/1995 | Hanna |
| 5,568,263 A | 10/1996 | Hanna |
| 6,252,661 B1 | 6/2001 | Hanna |
| 6,285,034 B1 | 9/2001 | Hanna et al. |
| 6,313,948 B1 | 11/2001 | Hanna |
| 6,787,724 B2 | 9/2004 | Bennett et al. |
| 6,959,108 B1 | 10/2005 | Bartelt et al. |

(Continued)

FOREIGN PATENT DOCUMENTS

WO 2005022076 A2 3/2005

OTHER PUBLICATIONS

International Search Report and Written Opinion; International application No. PCT/US2013/028591; dated Apr. 26, 2013.
Wilson, Andrew; "Lens Designs Tackle Novel Vision Applications"; Vision Systems Design; Jul. 1, 2011; URL: http://www.vision-systems.com/articles/print/volume-16/issue-7/features/lens-designs-tackle-novel-vision-applications.html.

(Continued)

*Primary Examiner* — Jamil Ahmed
(74) *Attorney, Agent, or Firm* — Brooks Kushman P.C.

(57) ABSTRACT

A high-speed, 3-D method and system for optically inspecting parts are provided. The system includes a part transfer subsystem including a transfer mechanism adapted to support a part at a loading station and transfer the supported part from the loading station to an inspection station at which the part has a predetermined position and orientation for inspection. The system also includes an illumination assembly to simultaneously illuminate an end surface of the part and a peripheral surface of the part. The system further includes a lens and detector assembly to form an optical image of the illuminated end surface and an optical image of the illuminated peripheral surface of the part and to detect the optical images. The system still further includes a processor to process the detected optical images to obtain an end view of the part and a 3-D panoramic view of the peripheral surface of the part.

1 Claim, 5 Drawing Sheets

(56) References Cited

U.S. PATENT DOCUMENTS

| | | | |
|---|---|---|---|
| 6,995,837 B1 | 2/2006 | Moir et al. | |
| 7,164,783 B2 | 1/2007 | Yang et al. | |
| 7,245,759 B2* | 7/2007 | Jones et al. | 382/152 |
| 7,403,872 B1 | 7/2008 | St. Onge et al. | |
| 7,491,319 B1 | 2/2009 | Yang | |
| 7,649,690 B2* | 1/2010 | Simkulet et al. | 359/627 |
| 7,669,707 B2 | 3/2010 | Kenneway | |
| 7,801,692 B2 | 9/2010 | Yang | |
| 2005/0174567 A1 | 8/2005 | Hanna | |
| 2006/0023105 A1 | 2/2006 | Kostrzewski et al. | |
| 2006/0140470 A1 | 6/2006 | Watanabe | |
| 2006/0236792 A1* | 10/2006 | Hanna | 73/865.8 |
| 2008/0182008 A1* | 7/2008 | Snow et al. | 427/8 |
| 2010/0245850 A1 | 9/2010 | Lee et al. | |
| 2010/0278417 A1* | 11/2010 | Yang | 382/152 |
| 2011/0220958 A1 | 9/2011 | Yoneda | |

OTHER PUBLICATIONS

International Search Report and Written Opinion; International application No. PCT/US2013/029484; dated May 10, 2013.
Office Action, U.S. Appl. No. 13/714,996; dated Apr. 10, 2014.
International Preliminary Report on Patentability; International Application No. PCT/US2013/028591; dated Sep. 18, 2014.
International Preliminary Report on Patentability; International Application No. PCT/US2013/029484; dated Sep. 18, 2014.
Notice of Allowance, U.S. Appl. No. 15/132,450, dated Jan. 30, 2017.
Notice of Allowance and Fee(s) Due; related U.S. Appl. No. 14/876,192; dated Mar. 31, 2016.
Final Office Action; related U.S. Appl. No. 14/722,329; dated Nov. 18, 2016.
Notice of Allowance and Fee(s) Due; related U.S. Appl. No. 14/876,187; dated Mar. 15, 2016.

* cited by examiner

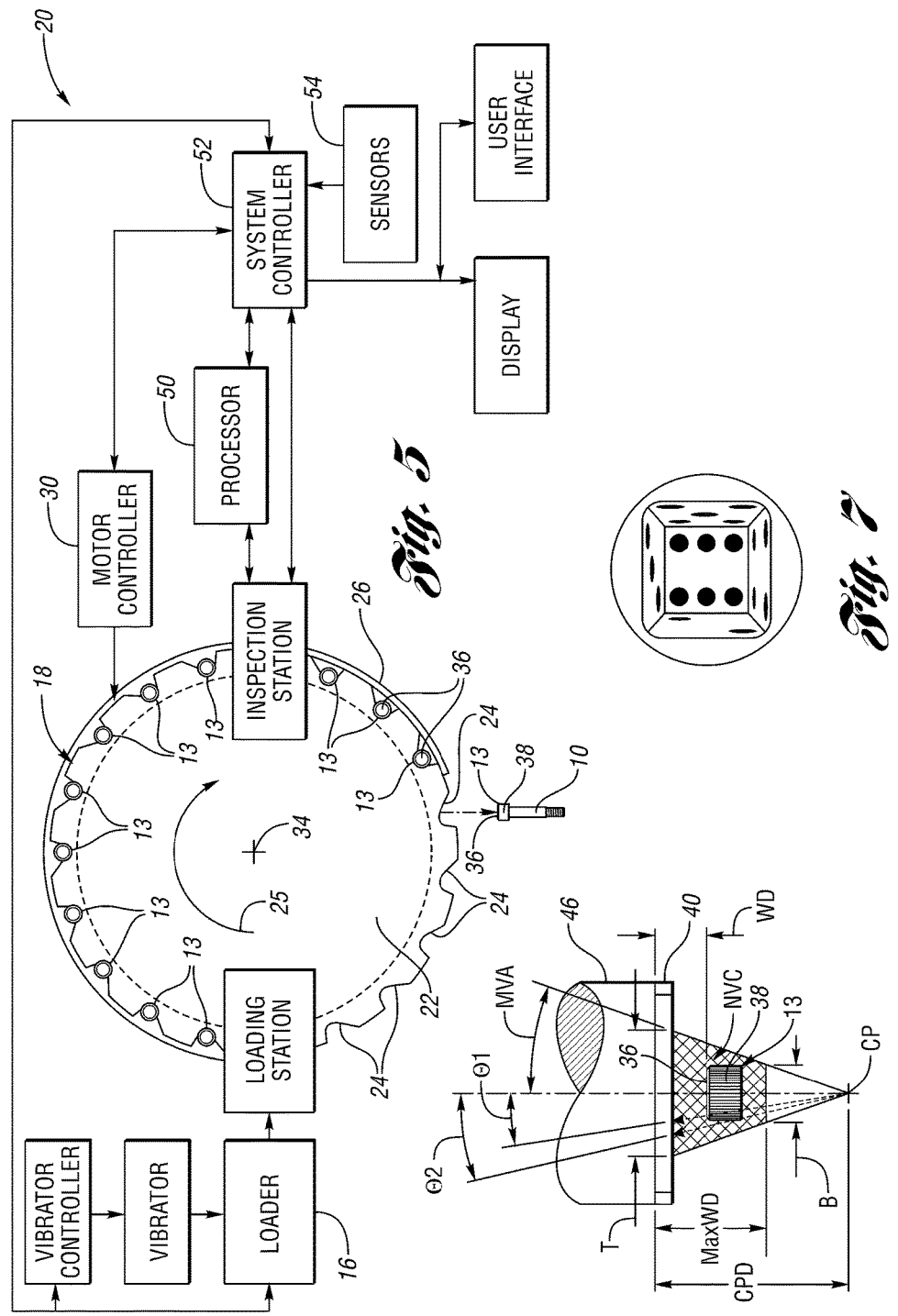

HIGH-SPEED, 3-D METHOD AND SYSTEM FOR OPTICALLY INSPECTING PARTS

TECHNICAL FIELD

This invention relates in general to the field of the non-contact, optical inspection of parts and, more particularly, to high-speed, 3-D methods and systems for optically inspecting parts, such as threaded fasteners.

Overview

Traditional manual, gauging devices and techniques have been replaced to some extent by automatic inspection methods and systems. However, such automatic inspection methods and systems still have a number of shortcomings associated with them.

Many parts, such as fasteners, are cold formed from wire stock. Oftentimes a crack or split results in the head of the part or fastener during such cold forming. Such cracks or splits can appear not only in the top surface of the head but also in the peripheral side surfaces of the head. Multiple cameras can be used to image these surfaces but that increases cost and space requirements of the inspection system. Also, the parts can be rotated about their axes but this adds additional time to the inspection process.

Metering wheels are often used in optical part inspecting and sorting systems. Such wheels separate the parts and can feed the separated parts on a "Vee" track. Prior metering wheels are typically made of UHMW or Delrin plastic.

Pericentric or hypercentric lenses suffer from cost, weight and size issues. As a result, linescan products are most commonly used to image fasteners: Linescan provides high resolution, distortion free images and good control over illumination. However, linescan-based systems also suffer from technical and cost concerns; parts to be inspected must be brightly illuminated and rotated within the camera's field of view (FOV).

U.S. Pat. No. 7,403,872 discloses a method and system for inspecting manufactured parts such as cartridges and cartridge cases and sorting the inspected parts.

WO 2005/022076 discloses a plurality of light line generators which generate associated beams of light that intersect a part to be inspected.

U.S. Pat. No. 6,313,948 discloses an optical beam shaper for production of a uniform sheet of light for use in a parts inspection system having a light source including a coherent light generator, a diffractive beam shaper, and lens elements.

U.S. Pat. No. 6,285,034 discloses an inspection system for evaluating rotationally asymmetric workpieces for conformance to configuration criteria.

U.S. Pat. No. 6,252,661 discloses an inspection system for evaluating workpieces for conformance to configuration criteria.

U.S. Pat. No. 6,959,108 discloses an inspection system wherein workpieces to be inspected are consecutively and automatically launched to pass unsupported through the field of view of a plurality of cameras.

U.S. Pat. No. 4,831,251 discloses an optical device for discriminating threaded workpiece by the handedness by their screw thread profiles.

U.S. Pat. No. 5,383,021 discloses a non-contact inspection system capable of evaluating spatial form parameters of a workpiece to provide inspection of parts in production.

U.S. Pat. No. 5,568,263 also discloses a non-contact inspection system capable of evaluating spatial form parameters of a workpiece to provide inspection of parts in production.

U.S. Patent Application Publication No. 2005/0174567 discloses a system to determine the presence of cracks in parts.

U.S. Patent Application Publication No. 2006/0236792 discloses an inspection station for a workpiece including a conveyor, a mechanism for rotating the workpiece, and a probe.

Other U.S. patent documents related to the invention include: U.S. Pat. Nos. 6,787,724; 6,995,837; 7,164,783; 7,245,759; 7,491,319; 7,669,707; and 7,801,692.

SUMMARY OF EXAMPLE EMBODIMENTS

An object of at least one embodiment of the present invention is to provide a high-speed, 3-D method and system to optically inspect parts without the need for multiple cameras and without the need for part rotation thereby providing a compact, cost-effective and simpler solution to the inspection task.

In one example embodiment, a high-speed, 3-D method of optically inspecting parts is provided. The method includes the steps of supporting a part to be inspected at a loading station and transferring the supported part so that the part travels along a first path which extends from the loading station to an inspection station at which the part has a predetermined position and orientation for inspection. The method further includes simultaneously illuminating an end surface of the part and a peripheral surface of the part at the inspection station and forming an optical image of the illuminated end surface and an optical image of the peripheral surface of the part at a single image plane at the same time. The method also includes detecting the optical images at the image plane and processing the detected optical images to obtain an end view of the part and a 3-D panoramic view of the peripheral surface of the part. The method still further includes transferring the part after the inspection at the inspection station so that the inspected part travels along a second path which extends from the inspection station to an unloading station.

The optical image of the illuminated end surface may be formed at a central portion of the image plane and the optical image of the peripheral surface may be formed around the central portion at the image plane.

The peripheral surface may be an outer peripheral surface which extends 360° around the part.

The loading station may be spaced away from the unloading station.

The method may further include the step of coordinating the inspection of the part at the inspection station with the transfer of the part to and from the inspection station to control movement of the part and the inspecting of the part.

The first and second paths may define a curved path wherein each of the stations is located along the curved path.

The method may further include processing the detected images to identify a defective part.

The radiation may be visible light radiation.

The parts may have heads wherein the end surface is a top surface of the head and wherein the peripheral surface is a peripheral surface of the head.

The detected optical images of the head may be processed to determine a head crack or split.

The parts may be fasteners.

In another example embodiment, a high-speed, 3-D system for optically inspecting parts is provided. The system includes a part transfer subsystem including a transfer mechanism adapted to receive and support a part at a loading station and to transfer the supported part so that the part travels along a first path which extends from the loading station to an inspection station at which the part has a predetermined position and orientation for inspection. The transfer mechanism transfers the part after inspection at the inspection station so that that the inspected part travels along a second path which extends from the inspection station to an unloading station. The system also includes an illumination assembly to simultaneously illuminate an end surface of the part and a peripheral surface of the part. The system further includes a lens and detector assembly to form an optical image of the illuminated end surface and an optical image of the illuminated peripheral surface of the part and to detect the optical images. The system further includes a processor to process the detected optical images to obtain an end view of the part and a 3-D panoramic view of the peripheral surface of the part.

The lens and the detector assembly may include a hypercentric or pericentric lens subsystem. The lens subsystem may provide a converging 3-D panoramic view of the peripheral surface of the part.

The peripheral surface may be an outer peripheral surface which extends 360° around the part.

The detector may include an image sensor having an image plane to detect the optical images.

The illumination assembly may include at least one source of radiation.

The parts may have heads wherein the end surface is a top surface of the head and the peripheral surface is a peripheral surface of the head.

The detected optical images may be processed to determine a head crack or split.

The parts may be fasteners.

The optical image of the illuminated end surface may be formed at a central portion of the image plane and the optical image of the peripheral surface may be formed around the central portion at the image plane.

The transfer mechanism may include a metering wheel.

The at least one source of radiation may include a backlight wherein the transfer mechanism is disposed between the lens and detector assembly and the backlight at the inspection station.

The metering wheel may be an optically transparent to permit the part to be imaged by the backlight through the metering wheel.

In yet another example embodiment, a high-speed, 3-D system for optically inspecting fasteners is provided. Each of the fasteners has a head. The system includes a fastener transfer subsystem including a transfer mechanism adapted to receive and support a plurality of fasteners at their heads in spaced apart relationship at a loading station and to transfer the supported fasteners so that the fasteners travel along a first path which extends from the loading station to an inspection station at which the fasteners have a predetermined position and orientation for inspection. The transfer mechanism transfers the fasteners after the inspection at the inspection station so that the inspected fasteners travel along a second path which extends from the inspection station to an unloading station. The system further includes an illumination assembly to simultaneously illuminate a top surface of the head and an entire peripheral surface of the head when the fastener is located at the inspection station. The system also includes a hypercentric or pericentric lens and detector assembly to form an optical image of the illuminated top surface and an optical image of the entire peripheral surface of the head and to detect the optical images. The system still further includes a processor to process the detected optical images to obtain a top view of the head and a 3-D panoramic view of the entire peripheral surface of the head and to determine a head crack or split.

The peripheral surface may be an outer peripheral surface.

Other technical advantages will be readily apparent to one skilled in the art from the following figures, descriptions and claims. Moreover, while specific advantages have been enumerated, various embodiments may include all, some or none of the enumerated advantages.

BRIEF DESCRIPTION OF THE DRAWINGS

FIG. 5 is a block diagram schematic view of the system of FIGS. 2-4 with its metering wheel at inspection, loading and unloading stations;

FIG. 6 is a side schematic view, partially broken away, of a hypercentric or pericentric lens and supported ring light with an object positioned within the near viewing cone (NVC) of the lens; and FIG. 7 shows top and side converging views of an object (here a dice) as it will appear at an image plane of an optical detector or camera after imaging through the lens of FIG. 6.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

In general, one embodiment of the high-speed, 3-D method and system of the present invention optically inspects manufactured parts such as fasteners or bolts illustrated in FIGS. 2-6. The inspected parts are then typically sorted based on the inspections. The system is designed for the inspection of the heads of such bolts for splits and/or cracks. However, the system is also suitable for other small, mass-produced manufactured parts where external splits and cracks are of concern. The subsystems which may be used for part handling and delivery may vary widely from application to application depending on part size and shape, as well as what inspections are being conducted. The subsystems ultimately chosen for part handling and delivery have some bearing on the nature of the subsystem or system conducting the optical inspection.

Figure 1:
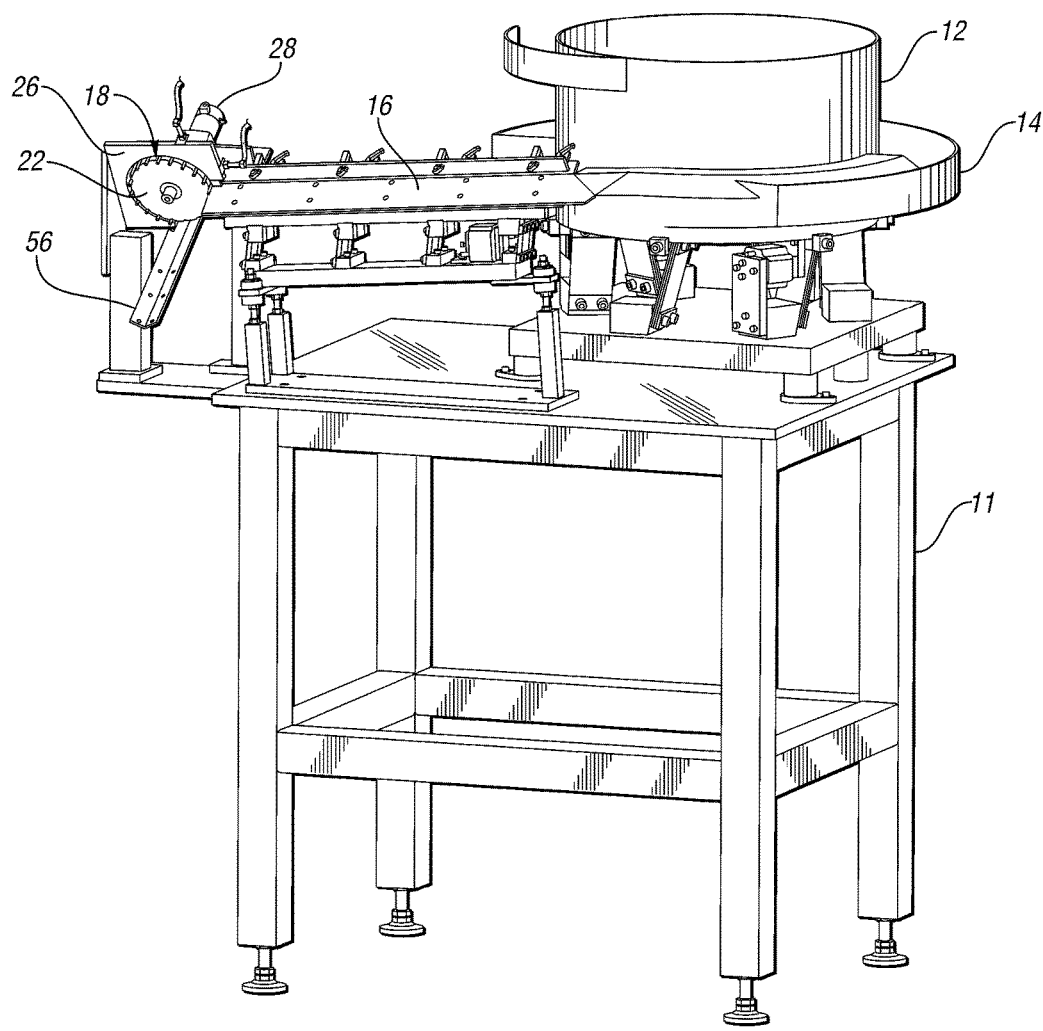
FIG. 1 is a perspective environmental view of at least one embodiment of a high-speed, 3-D system for optically inspecting parts.
Figure 2:
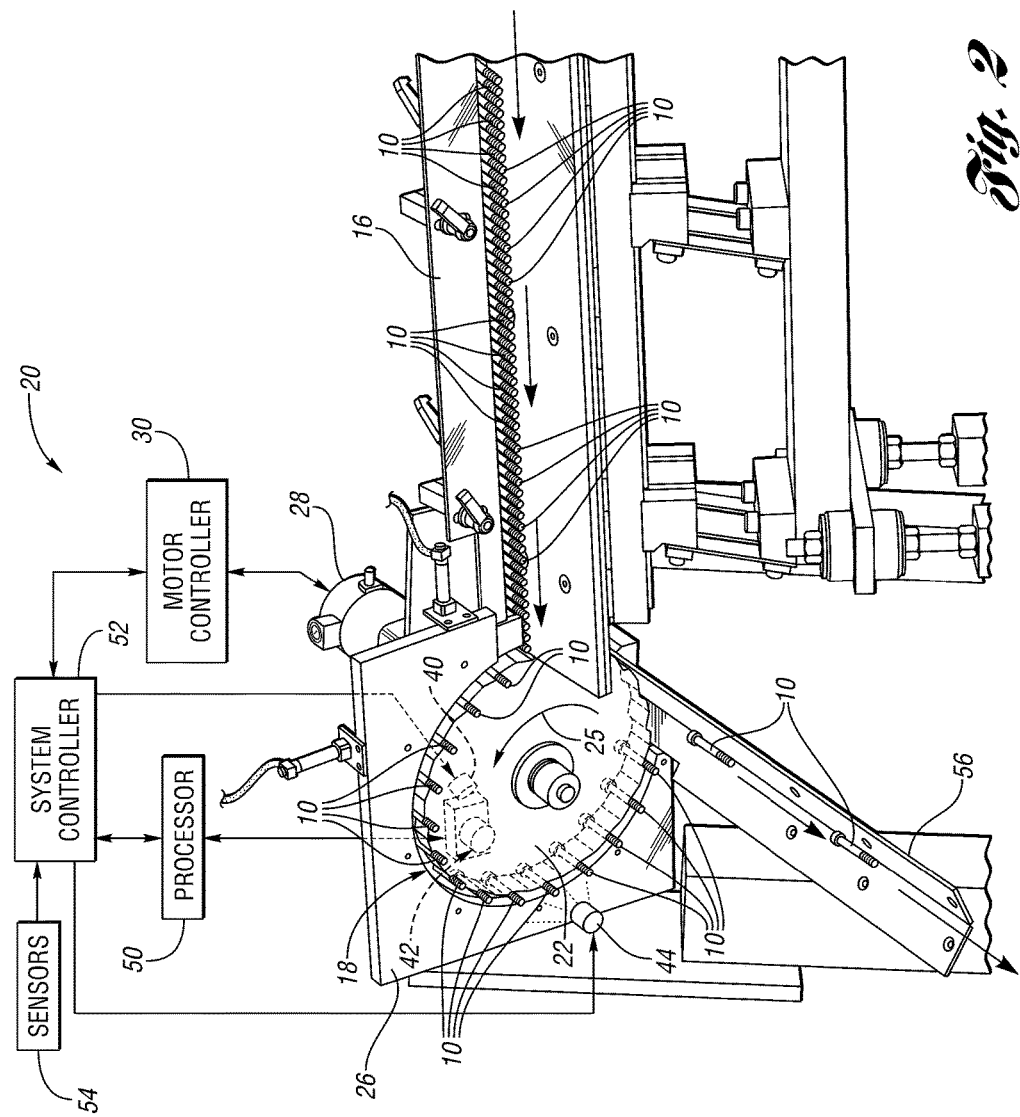
FIG. 2 is an enlarged top side perspective, block diagram view, partially broken away, of the system of FIG. 1.
Figure 3:
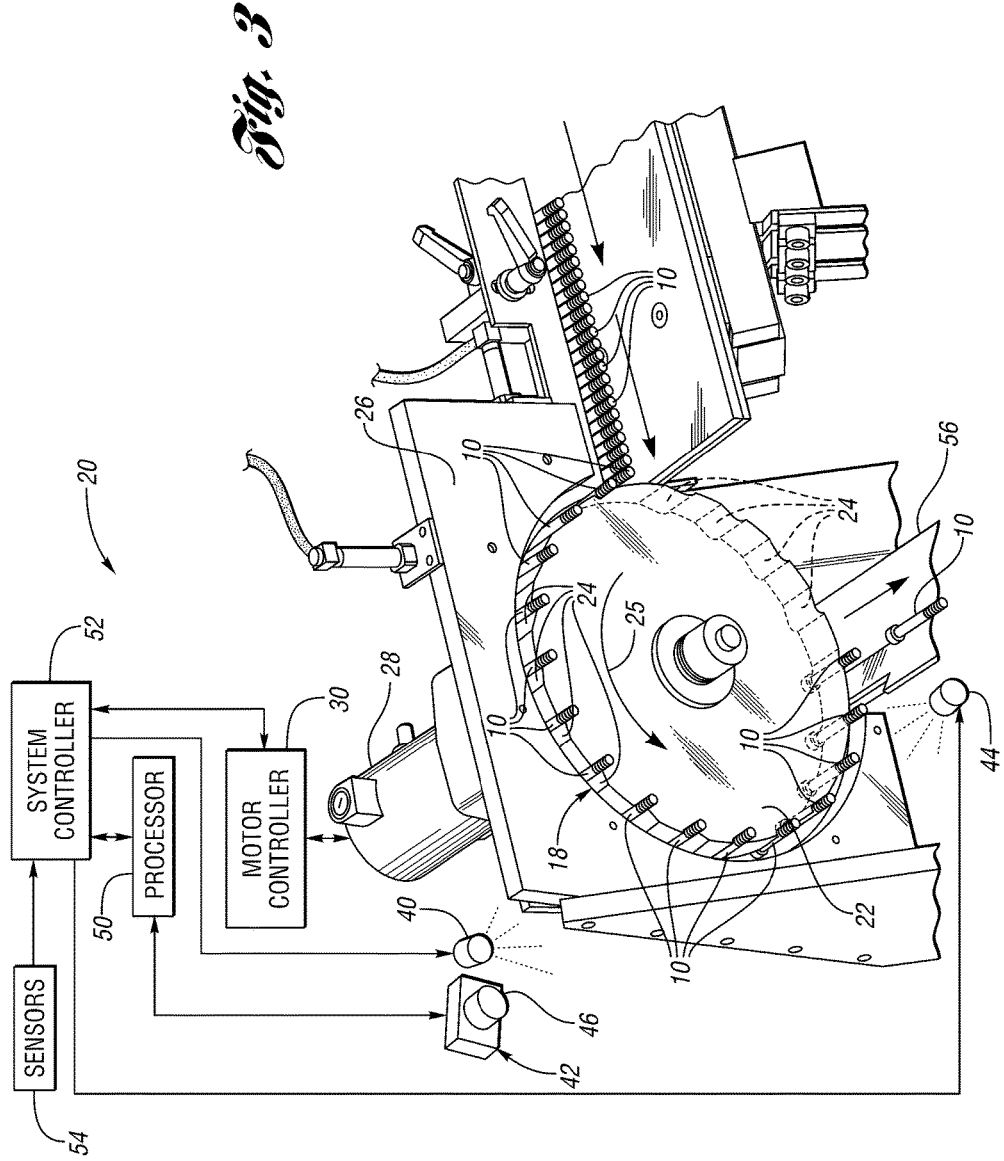
FIG. 3 is a top side perspective block diagram view, partially broken away, and opposite the side of FIG. 2 of the system of FIGS. 1 and 2.
Figure 4:
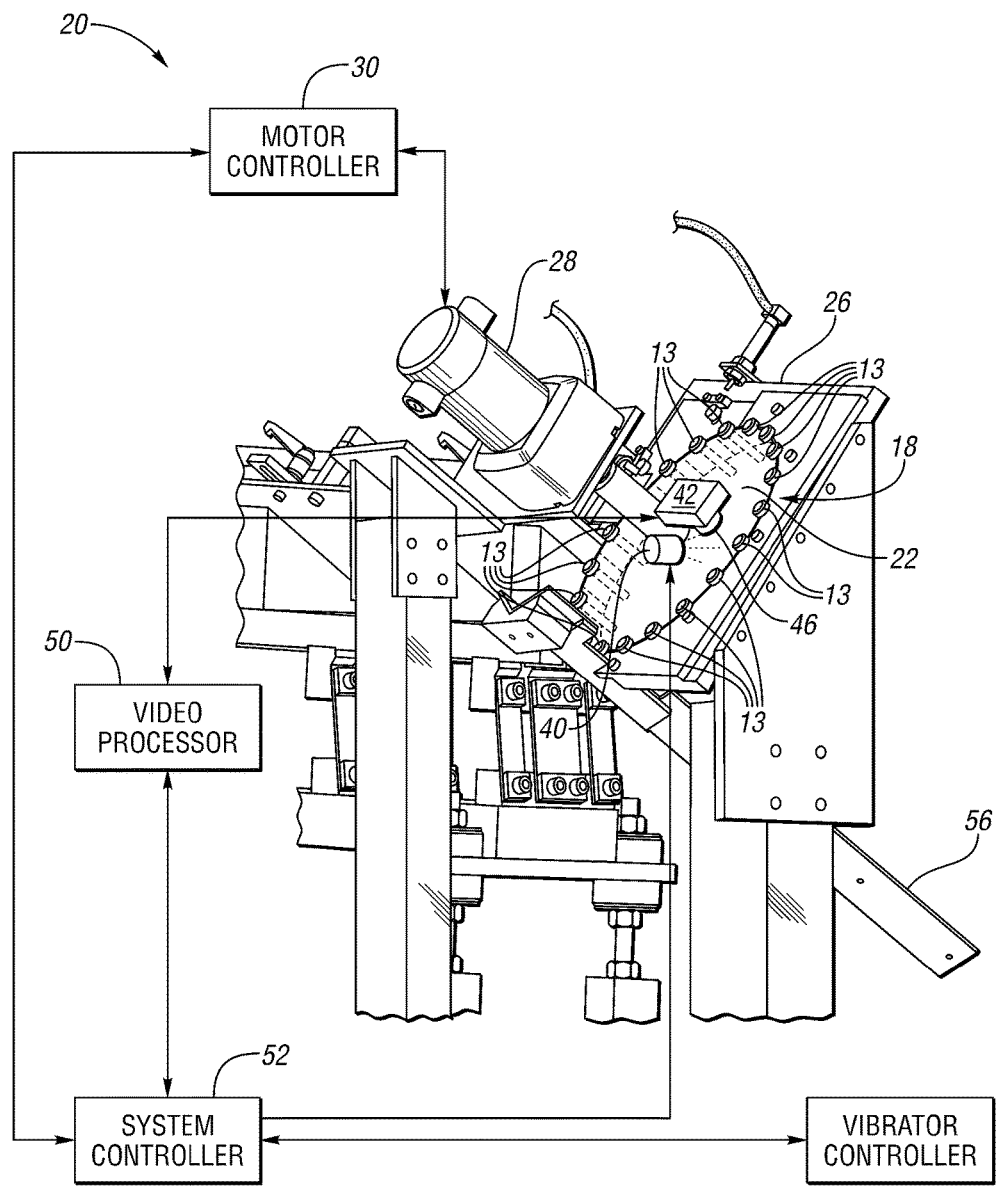
FIG. 4 is a back side perspective block diagram view of the system of FIGS. 1, 2 and 3.

Initially, parts, such as bolts 10 (FIGS. 2-6), are placed into a feeder bowl 12 having a scalloped rim 14. The bowl 12 is supported on an adjustable frame structure 11. Tooling around the rim 14 takes advantage of the asymmetrical mass distribution of the bolts 10 to feed the bolts 10 onto a downwardly sloped vibratory feeder conveyor or loader 16. Consequently, every bolt 10 which exits the bowl 12 is received by the conveyor 11 and is oriented in the same direction as shown in FIGS. 2 and 3. One or more vibrators controlled by a vibrator controller (FIG. 5) vibrate the bowl 12 and the conveyor 11 to help move the bolts 10 in single file to a loading station (FIG. 5). At the loading station the longitudinal axes of the bolts 10 are substantially parallel.

At the loading station, a part transfer subsystem, generally indicated at 18, of a high-speed, 3-D system 20 for optically inspecting parts is provided to transfer the bolts from the loading station, to an inspection station and then to an unloading station. The subsystem 18 includes a transfer mechanism in the form of metering wheel 22 which is, preferably, made of an optically transparent plastic material such as acrylic so that heads 13 of the bolts 10 (FIGS. 5 and 6) can be backlight only or backlight/frontlight simultaneously during imaging as described in detail herein below. If the inspection application needs a black or white background, a different wheel can be chosen for the different colored bolt head.

The wheel 22 has openings 24 formed about its outer peripheral surface which are adapted to receive and support the bolts 10 at the loading station and to transfer the supported bolts 10 so that the bolts 10 travels along a first path indicated by an arrow 25 which extends from the loading station to an inspection station (FIG. 5) at which each bolt 10 has a predetermined position and orientation for optical inspection. The bolts 10 are supported on the wheel 22 during wheel rotation by a stationary guide 26. The wheel 22 is rotated by an electric motor 28 under the control of a motor controller 30 to rotate about an axis 34 (FIG. 5).

At the inspection station, each bolt axis is aligned with an optical axis of a hypercentric or pericentric lens as described in detail below. Consequently, axial or on-axis machine vision viewing is provided. After inspection, the wheel 22 transfers the bolts 10 from the inspection station so that the inspected bolts 10 travel along a second path which extends from the inspection station to an unloading station where the now unsupported bolts 10 fall under the force of gravity.

The system 20 also includes an illumination assembly to simultaneously illuminate an end surface 36 of each bolt head 13 and an outer peripheral surface 38 of each bolt head 13. The illumination assembly typically includes an LED ring light 40 (FIG. 6) on or adjacent a lens and detector assembly, generally indicated at 42, and which has an optical axis. The illumination assembly also typically includes a backlight 44 which illuminates the bolt heads 13 through the optically transparent wheel 22.

The lens and detector assembly 42 forms an optical image of the illuminated end surface 36 and a converging optical image of the illuminated peripheral surface 38 of the bolt head 13 and detects the optical images. The assembly 42 includes a detector in the form of an image sensor having an image plane to detect the optical images.

The assembly 42 preferably has a pericentric or hypercentric lens subsystem 46 wherein the lens subsystem provides a converging 3-D panoramic view of the outer peripheral surface 38 of each bolt head 13. The surface 38 extends 360° around the bolt head 13. For illustrative purposes only, FIG. 7 shows an imaged peripheral surface of a die having faces "3", "5", "4" and "2" which surround a top surface of the die face, "6".

The system 20 also includes a video processor 50 to process the detected optical images to obtain an end view of the bolt head 13 and a 3-D panoramic view of the peripheral surface 38 of the bolt head 13. The detected optical images are processed by the processor 50 to determine a head crack or split. The processor 50 determines if a significant crack or split is present by seeing if the imaged light is discontinuous at a position corresponding to the crack location.

The system 20 also includes a system controller 52 which controls and coordinates the inspection of bolts 10 at the inspection station with the transfer of the bolts 10 and from the inspection station to control movement of the bolts 10 and the inspection of the bolts 10. The results of the processing by the processor 50 are output to the system controller 52 which controls the system 20 based on the results of the optical inspection. Sensors 54 provide various timing or position signals to the controller 52 to help control the system 20. For example, one type of sensor may signal the controller 52 when the bolts 10 are located at or near the inspection station in the system 20 so that the lens and detector assembly 42 can be controlled by the controller 52 to take "pictures" of the bolt heads 13 at the inspection station.

The system 20 may also include a display and a user interface (FIG. 5) to permit two-way user interaction with the system 20.

After inspection at the inspection station, the bolts 10 may be dropped onto a track 56 which may take the form of an AMPCO 18 oriented at a 35° angle. As the bolts 10 slide down the track 56, they may pass through other inspection stations to be inspected one at a time. Bolts 10 which pass each of the inspections may be actively accepted by a part diverter or flipper (not shown) located at the bottom of the track 56.

Referring now to FIG. 6, there are illustrated specifications for one type of hypercentric lens subsystem entitled "Hyper-Eye" available from Light Works, LLC of Toledo, Ohio. Hyper-Eye hypercentric lenses provide a converging view as if aimed at a single point called the Convergence Point (CP). The lenses can also provide a top view. The distance to this point is called the Convergence Point Distance (CPD).

The volume that can actually be well-imaged is contained within an imaginary truncated cone called the New View Cone (NVC). This is the hatched region of FIG. 6. The dimensions of this region are T, B and Max WD; WD is the distance from the lens 46 to the top surface 36 of the bolt head 13; these will vary for different lens models.

An additional parameter of Hyper-Eye lenses is the Maximum View Angle (MVA). This is the largest angle of the NVC. Rays of light from an object are collected over a broad range of angles, up to the limit of the MVA. Outside this angle, nothing is imaged.

The rays of light collected from the bolt head 13 are imaged at the detector. Larger ray angles correspond to larger image radii. This correspondence or Angle to Image Mapping (AIM) varies with the lens model. Obviously, other types of hypercentric lenses could also be used.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A high-speed, 3-D system for optically inspecting cold formed parts which have heads, the system comprising:

a part transfer subsystem including a transfer mechanism having a metering wheel adapted to receive and support a cold formed part at a loading station and to automatically transfer the supported part so that the part travels along a first path which extends from the loading station to an inspection station at which the head of the part has a predetermined position and orientation for inspection and to transfer the part after inspection at the inspection station so that the inspected part travels along a second path which extends from the inspection station to an unloading station;

an illumination assembly including at least one source of radiation which includes a backlight to simultaneously and automatically illuminate a top surface of the head and an outer peripheral surface which extends 360° around the head, and, wherein the metering wheel is optically transparent to permit the head to be imaged by the backlight through the metering wheel;

a lens and detector assembly to generate a signal indicating the part is in position for the top surface and the peripheral surface of the head to be optically inspected and, based on the generated signal, form an optical image of the illuminated top surface and an optical image of the illuminated peripheral surface of the head and to detect the optical images, wherein the at least one source of radiation includes a backlight wherein the transfer mechanism is disposed between the lens and detector assembly and the backlight at the inspection station, and wherein the optical image of the illuminated top surface is formed at a central portion of the image plane and the optical image of the peripheral surface is formed around the central portion at the image plane; and a processor to process the detected optical images to obtain an end view of the part and a 3-D panoramic view of the peripheral surface of the head to determine a head crack or split and to identify a defective part having the head crack or split appearing in the peripheral surface of the head and caused by the cold forming.

* * * * *